US007033573B2

(12) United States Patent  
Morita

(10) Patent No.: US 7,033,573 B2
(45) Date of Patent: Apr. 25, 2006

(54) DIAGNOSES AND TREATMENT OF DISORDERS USING AN ALTERNATIVE GLUCOSE PATHWAY

(76) Inventor: Kieko Morita, 15434 Sherman Way, #2-324, Van Nuys, CA (US) 91406

( * ) Notice: Subject to any disclaimer, the term of this patent is extended or adjusted under 35 U.S.C. 154(b) by 0 days.

(21) Appl. No.: 10/665,117

(22) Filed: Sep. 22, 2003

(65) Prior Publication Data

US 2004/0057901 A1   Mar. 25, 2004

Related U.S. Application Data

(63) Continuation of application No. 09/854,298, filed on May 9, 2001, now abandoned.

(60) Provisional application No. 60/202,967, filed on May 10, 2000.

(51) Int. Cl.
*A61K 49/00* (2006.01)
(52) U.S. Cl. .................................. 424/9.1; 424/9.2
(58) Field of Classification Search ............... 424/1.11, 424/9.1, 9.2, 9.3, 9.4–9.8; 514/167, 169
See application file for complete search history.

(56) References Cited

U.S. PATENT DOCUMENTS 6,369,046 B1 *   4/2002   Schatzberg et al. ......... 514/167
6,620,802 B1      9/2003   Schatzberg et al. ......... 514/178

OTHER PUBLICATIONS

Swaab et al, Jornal of Neuroendocrinology, 1994, vol. 6, pp. 681-687.*
Peskind et al, Neurology, 2001, vol. 56, pp. 1094-1098.*
Joseph K. Belanoff et al., "slowing the Progression of Cognitive Decline in Alzheimer's Disease Using Mifepristone", *Journal of Molecular Neuroscience*, vol. 19, 2002, pp. 201-206.
Linda E. Carlson et al., "Relationships between Dehydroepiandrosterone Sulfate (DHEAS) and Cortisol (CRT) Plasma Levels and Everyday Memory in Alzheimer's Disease Patients Compared to Healthy Controls", *Hormones and Behavior 35*, 1999, pp. 254-263.
Michael T. Falduto et al., "Role of Apolipoprotein E in Neurobiology and the Pathogenesis of Alzheimer's Disease", *Pharmacological Treatment of Alzheimer's Disease*, 1997 Chapter 12, pp. 287-307.
Suzanne Craft, PhD et al., "Enhancement of Memory in Alzheimer Disease With Insulin and Somatostatin, but Not Glucose", *Arch Gen Psychiatry* vol. 56 Dec. 1999, pp. 1135-1140.
Segal MB., "Transport of Nutrients Across the Choroid Plexus", *Microsc Res Tech*, 2001, 52(1): 38-48, National Library of Medicine (PubMed, Abstract only).

Sommer JB et al., "Does lumbar cerebrospinal fluid reflect ventricular cerebrospinal fluid? A prospective study in patients with external ventricular drainage", *Eur Neurol*, 2002, 47(4): 224-32, National Library of Medicine (PubMed, Abstract only) (Oct. 2002).
"Insulin, Neurogentics and Memory in Alzheimer's Disease", *Clinical Trials.gov.*, Department of Veterans Affairs Medical Research Service Oct. 1999.
"The Evaluation and Follow-up of Patients with Memory Disorder and Normal Volunteers", *Clinical Trials.gov.*, National Institute of Mental Health Mar. 21, 1995.
Craft et al., "Insulin Metabolism in Alzheimer's . . . ", *Neuroendocrinology*, 1999; 70, pp. 146-152.
Craft et al., "Steroid-induced Elevation of Glucose . . . ", *Psyconeuroendocrinology* 28, 2003, pp. 113-120.
Craft et al., "Enhancement of Memory in . . . ", *Arch Gen Psychiatry*, vol. 56, Dec. 1999, pp. 1135-1140.
Craft et al., "Memory Improvement Following . . . ", *Neurobiology of Aging*, vol. 17, 1996, pp. 123-130.
Craft et al., "The Role of Insulin Resistance . . . ", *CNS Drugs*, 2003, 17, pp. 27-45.
Craft et al., "Insulin Effects on . . . ", *Annals of the New York Academy of Sciences* 903, 2000, pp. 222-228.
Luijpen et al., "Effects of Transcutaneous . . . ", *Neurorehabilitation and Neural* . . . 18(3), 2004, pp. 166-175.
Verhaagen et al., "Neurotrophin Receptors in . . . ", *Progress in Brain Research*, vol. 117, pp. 25 and 72.
Seiger et al., "Intracranial Infusion of Purified . . . ", *Behavioural Brain Research*, 57, 1993, pp. 255-261.
Fanelli et al., "Long-term Recovery from Unawareness . . . ", *Diabetologia* 37, 1994, pp. 1265-1276.
Pagano et al., "An in Vivo and in Vitro Study of . . . ", *J. Clin. Invest.*, vol. 72, 1983, pp. 1814-1820.
Park et al., "Intracerebroventricular . . . ", *Physiology & Behavior*, vol. 68, Issue 4, Feb. 2000 (Abstract).
Olson et al., "Nerve Growth Factor . . . ", *Journal of Neural Transmission* 4, 1992, pp. 79-95 (Summary).
Elrod et al., "Effects of Alzheimer's Disease . . . ", *Am. J. Psychiatry* 154:1, Jan. 1997 (Abstract page).
Wolkowitz et al., "DHEA Treatment of . . . " *Neurology* 2003; 60, pp. 1071-1076 (Abstract page).
Wu et al., "Molecular Changes . . . ", *Journal of Clinical . . .* 88 (12) pp. 5896-5906 (Abstract page).

* cited by examiner

*Primary Examiner*—Dameron L. Jones
(74) *Attorney, Agent, or Firm*—Westerman, Hattori Daniels & Adrian LLP

(57) ABSTRACT

This invention proposes the existence of an alternate glucose pathway different from that presently accepted and offers different methods of proving this. The proposed alternate glucose pathway considers the cerebral spinal fluid as a major component of the pathway. Based on this, a diagnostic tool for detecting mental disorders and neurological disorders which can not be detected by CT Scan and MRI is proposed. Medications directed at the CSF are also proposed.

1 Claim, 2 Drawing Sheets

DIAGNOSES AND TREATMENT OF DISORDERS USING AN ALTERNATIVE GLUCOSE PATHWAY

This patent application is a continuation of application Ser. No. 09/854,298 filed May 9, 2001 now abandoned, and claims the benefit of the priority of provisional application Ser. No. 60/202,967 filed May 10, 2000, both of which are hereby incorporated by reference.

BACKGROUND

Glucose metabolism is important for normal cellular process. It produces neurotransmitters and adenosine triphosphate (ATP), giving brain cells the energy to perform their normal function. Adequate glucose supply is essential for consciousness and cognitive functions indicating that glucose is critical for the normal operation of the mind, memory, and emotion. Conventional belief is that glucose is supplied to the brain by two pathways working in conjunction with each other. The first pathway supplies glucose from plasma within the capillaries inside the brain to the astrocytes where glycolysis takes place which then feeds lactate into the neurons. The first pathway mainly involves the whole cerebral cortex. The second pathway transports the glucose as well as insulin present in the plasma within the capillaries, hereinafter referred to as plasma glucose and plasma insulin respectively, to the spaces between the blood and brain side of the blood brain barrier, hereinafter referred to as BBB, to the brain's interstitial fluid which then carries the glucose and insulin to the brain proper. This second pathway also involves the whole cerebral cortex. The proponents of this second pathway do not consider the cerebral spinal fluid, hereinafter CSF, as a major component or factor of that pathway. The rationale given by the proponents of this second pathway is the observed low glucose concentration found in the CSF. This low glucose concentration is presently explained by a leakage of glucose to the CSF while the main flow of glucose occurs between the blood and brain side of the BBB.

These pathways do not however explain all of the phenomena occurring in the brain. The proceeding are some of the unexplained phenomena:

A. The absence of the correlation between the glucose metabolism and the cerebral blood flow (Suda, S., Shinohara, M., Miyaoka, M., Lucignani, G., Kennedy, C., & Sokoloff, L. The lumped constant of the deoxyglucose method in hypoglycemia: effects of moderate hypoglycemia on local cerebral glucose utilization in the rat. Journal of Cerebral Blood Flow and Metabolism, 10, pp. 499–509. 1990. International Society for Cerebral Blood Flow and Metabolism. Bethesda, Md. 20892-1180).

B. Uneven glucose distribution in the cortex after severe hypoglycemia episode (Agrdh, C.-D., Kalimo, H., Olsson, Y., and Siesjo, B. K. Hypoglycemia brain injury. Acta Neuropathologica, 50, pp. 31–41. 1980. Springer-Verlag. Heidelberg, Germany; Kalimo, H. & Olsson, Y. Effects of severe hypoglycemia on the human brain. Acta Neurologica, 62, pp. 345–356. 1989. Munksgaard International Publishers Ltd. New York, N.Y.).

C. Different types of cell injuries under severe hypoglycemia (Agrdh, C.-D., Kalimo, H., Olsson, Y., and Siesjo, B. K. Hypoglycemia brain injury. Acta Neuropathologia, 50, pp. 31–41. 1980. Springer-Verlag. Heidelberg, Germany).

D. Different recovery rates in the brain cells after severe hypoglycemia followed by glucose injection (Agrdh, C.-D., Kalimo, H., Olsson, Y., and Siesjo, B. K. Hypoglycemia brain injury. Acta Neuropathologia, 50, pp. 31–41. 1980. Springer-Verlag. Heidelberg, Germany).

E. Different survival rates in the brain cells after severe hypoglycemia (Agrdh, C.-D., Kalimo, H., Olsson, Y., and Siesjo, B. K. Hypoglycemia brain injury. Acta Neuropathologia, 50, pp. 31–41. 1980. Springer-Verlag. Heidelberg, Germany).

F. The relation between the thyroid hormones and mental disturbance (Bauer, M. S. & Whybrow, P. C. Thyroid hormones and the central nervous system in affective illness: interactions that may have clinical significance. Integrative Psychiatry, 6, pp. 75. 1988. Elsevier Science Publishing Co., Inc. New York, N.Y. 10017; Joffe, T. R., Sokolov, T. H. S. Thyroid hormones, the brain, and affective disorders. Critical Reviews in Neurobiology, 8, pp. 45–63. 1994. Begell House, Inc. Congers, N.Y. 10920).

G. How the cerebral spinal fluid flows against gravity from the choroid plexus to the sagittal sinus (Nolte, J. The Human Brain: An Introduction to Its Functional Anatomy, pp. 85. 1999. Mosby-Year Book, Inc. St. Louis, Mo. 63146).

H. Ventricular enlargement observed in dementia (Rao, C. V. G. K. Degenerative disease and hydrocephalus. Cranial MRI and CT, pp. 181–259. 1999. Mc Graw-Hill. New York. N.Y.) and in severe hypoglycemia (Kalimo, H & Olsson, Y. Effects of severe hypoglycemia on the human brain. Acta Neurologica Scandinavica, 62, pp. 345–356. 1989. Munksgaard International Publishers Ltd. Malden, Mass. 02148-5018)

I. Apoptosis in Alzheimer's disease (Connor, B. & Dragunow, M. The role of neuronal growth factors in neurodegenerative disorders of the human brain. Brain Research Review, 27, pp. 1–39. 1998. Elsevier/North-Holland Biomedical press. Amsterdam, Netherlands).

J. Lower CSF insulin and higher plasma insulin in more advanced Alzheimer's disease (Craft, S., Peskind, E., Schwartz, M. W., Schellenberg, G. D., Raskind, M., & Porte, D. Jr. Cerebrospinal fluid and plasma insulin levels in Alzheimer's disease: relationship to severity of dementia and apolipoprotein E genotype. Neurology, 50, pp. 164–168. 1998. The American Academy of Neurology. Lippincott Williams & Wilkins, Inc. St. Paul, Minn. 55116).

K. Beta-amyloid precursor protein abnormality in Alzheimer's disease (Cerebromicrovascular pathology In Alzheimer's disease compared to normal aging. Gerontology, 43. 1997. S. Karger Publishers, Inc. Farmington, Conn.).

L. Tau protein abnormality in Alzheimer's disease (Cerebromicrovascular pathology in Alzheimer's disease compared to normal aging. Gerontology, 43. 1997. S. Karger Publishers, Inc. Farmington, Conn.).

M. Altered peptidase activities in Alzheimer's disease (Yasuda M, Maeda K, Kakigi T, Minamitani N, Kawaguchi T, & Tanaka T. Neuropeptides, 29. 1995. Harcourt Brace & Co. Ltd. Kent DA145 HP).

N. Abnormal neuropeptides in Alzheimer's disease (Heiling M, Sjogren M, Blennow K, Ekman R, & Wallin A. Biological Psychiatry, 38. 1995. Elsevier Science Inc. New York, N.Y. 10010-5107; Sekiya K, Haiji M, Fukahori M, Takahanagi R, Ohashi M, Kurose S, Oyama M, Tateishi K, Funakoshi A, & Nawata H. Neuroscience Letters, 177. 1994. Elsevier Science Ltd. New York, N.Y. 10010).

O. The reason for the inability of CT scan and Magnetic Resonance Imaging (MRI) to detect mental illnesses and neuro degenerative diseases.

This invention shows that the above unexplained phenomena occurring in the brain is due to the presence of an alternate glucose pathway different from the second pathway described above. This alternate glucose pathway also works in conjunction with the first pathway and an insulin pathway occurring at the cortex cell layer I–III, possibly IV, in the brain and the spine. The presence of elevated levels of some biological materials in the CSF like cortisol, the uneven distribution of glucose in the cerebral cortex and the uneven damage observed on the brain cells under severe hypoglycemia, the absence of correlation between the glucose metabolism and the cerebral blood flow (CBF) are just some observation that justifies the existence of the proposed alternate glucose path way. This alternate glucose pathway when applied in conjunction with the other pathways explains the motor function, the functions of memory, mind and emotion, the effect of the thyroid hormones to mental disorders, dementia in cerebral ischemic infarction, hypoglycemia, Alzheimer disease, autism, dementia, and psychiatric illness.

It is therefore an object of this invention to show the presence of an alternate glucose pathway.

It is also an object of this invention to show the importance of collecting and testing the CSF for the diagnoses of mental disorders and those disorders related to neurological illnesses which can not be diagnosed through Computed Tomography (CT scan) or Magnetic Resonance Imaging (MRI), hereinafter referred to as nondetectable neurological disorders. The mental disorders and nondetectable neurological disorders are collectively referred to herein as disorders.

It is also an object of this invention to provide a method for proving the presence of an alternate glucose pathway.

It is a further object of this invention to show that the alternate glucose pathway working in conjunction with the other pathways, explains the unexplained phenomena enumerated above.

It is likewise an object of this invention to provide an objective test for detecting mental disorders and nondetectable neurological disorders.

It is also an object of this invention to provide effective medications or facilitate the isolation or synthesis of effective medications utilizing the concept of this invention.

It is also an object of this invention to show that a medication to treat disorders should be readily available from the CSF.

DESCRIPTION OF THE INVENTION

Figure 1:
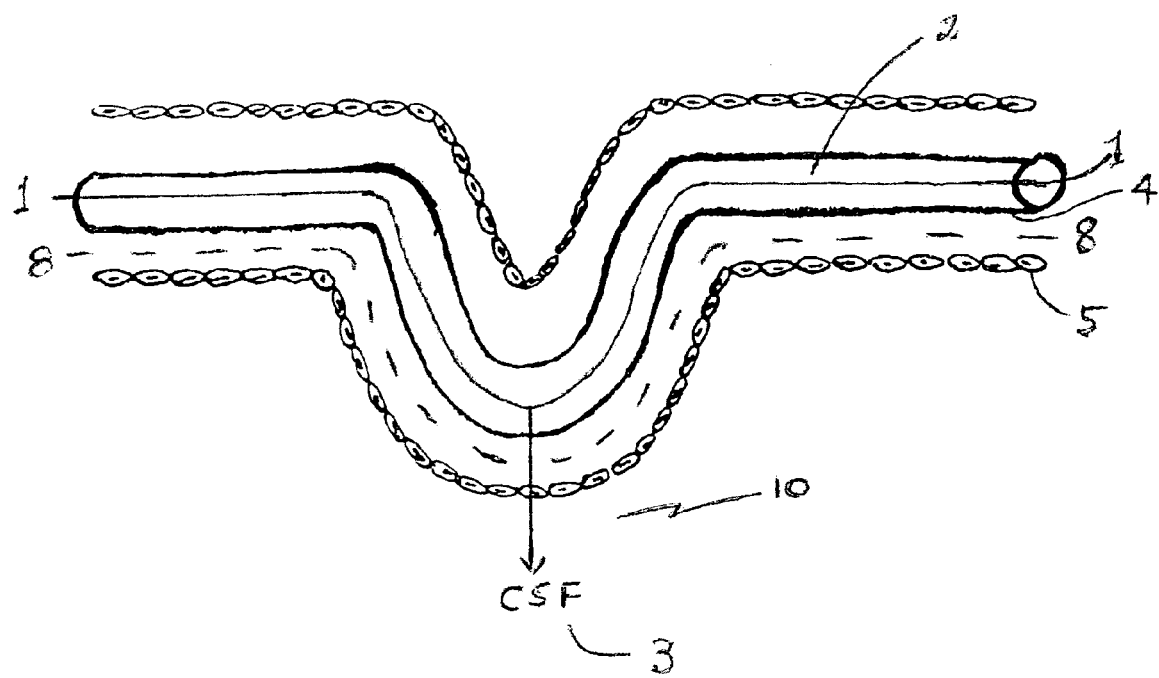
FIG. 1 shows the alternate glucose pathway in the blood brain barrier.
Figure 2:
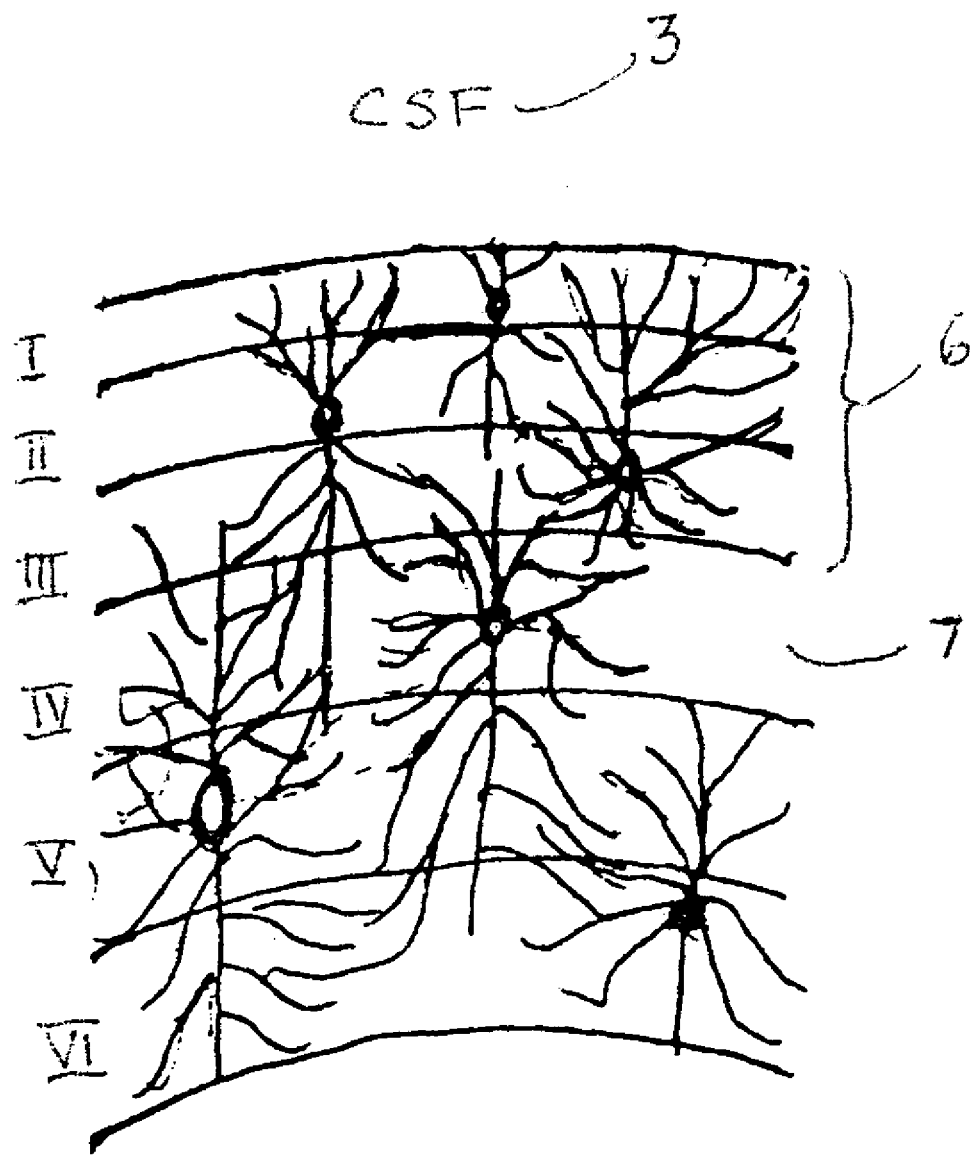
FIG. 2 shows the different cortex layers in relation to the cerebral spinal fluid.

The invention shows the presence of an alternative glucose pathway different from that proposed by the second pathway. This pathway works in conjunction with the first pathway and an insulin pathway, also proposed in this invention. In the alternative glucose pathway 10, glucose 1 present in the plasma within the capillaries 2 mainly flows directly to the CSF 3 passing through both the blood side 4 and the brain side 5 of the BBB to the cortex cell layer I–III 6 and possibly IV 7 of the brain and the spine as shown in FIGS. 1 and 2. The cortex cell layer I–III 6 consists mostly of dendritis and long axons, small pyramidal cells and pyramidal cells. Closely related to the alternate glucose pathway is an insulin pathway, not presently fully understood, which acts in conjunction with the alternate pathway and the first pathway to explain phenomena not adequately addressed by the present accepted pathways mentioned above. The claimed alternate glucose pathway 1 with the insulin pathway show that the CSF is a major factor or component of the pathways involved with the glucose transport in the cells within the cortex cell layers I–III 6, and possibly IV 7 in the brain and spine. In the claimed alternate glucose pathway, the rate of glucose metabolism in the cortex cell layer I–III and possibly layer IV in the brain, is high or fast which explains the low glucose concentration in the CSF even if the plasma glucose flows mainly to the CSF and not between 8 the blood 4 and brain side 5 of the BBB as is the current belief. This fast rate of metabolism in the cortex cell layer I–III and possibly IV, in the brain is explained by the effect of the thyroid hormone on the insulin pathway. In the insulin pathway, the insulin produced by the cells inside the cortex cell layer I–III of the brain and the spine partly binds to the insulin receptors on the outer membrane of the cells within the cortex cell layer I–III in the brain and spine with another part releasing to the CSF by the autocrine/paracrine relationship. The part of insulin that binds to the insulin receptor produces a signal to the nucleus of the cells within the cortex cell layer I–III in the brain which triggers the translation of DNA to RNA, the RNA consequently transcribing and producing glucose transporters concentrating at the cell membrane of the cells within the cortex cell layer I–III of the brain. The presence of these glucose transporters together with the glycolysis enzymes in the mitochondria of the cells within the cortex cell layer I–III of the brain allow glucose to more rapidly get into the inside of the cells within the cortex cell layer I–III of the brain which explains the low glucose concentration seen in CSF. The glucose inside the cortex cell layer I–III is metabolized by glycolysis. Due to the major role played by the CSF in the claimed pathway, the CSF should be the sample of choice for testing the presence of mental disorders such as Alzheimer Disease, Schizophrenia, dementia, Epilepsy, seizure disorders, bipolar disorders, mania, depression, and autism and neurological disorders which can not be detected by CT scan and MRI, i.e., the nondetectable neurological disorders, such as multiple sclerosis, Parkinson disease, Huntington's disease, and Systemic Lupus Erythematosus.

The invention also describes methods of proving the presence of an alternate glucose pathway. One method of proving the existence of the alternate glucose pathway comprises: drawing a small sample of CSF, blood and urine; testing the CSF, blood and urine samples for glucose concentration and for a component of CSF, hereinafter component, that has equal ability to flow within the BBB and the CSF, is an insulin counterregulatory hormone and is not produced by the brain such as cortisol; infusing the component into the vein; testing the CSF, blood and urine samples for glucose concentration and for the component of CSF after the infusion; and, comparing the glucose concentration and the concentration of the component in the CSF before and after the infusion into the vein.

An increase in concentration of both glucose and the component in the CSF and confirms the presence of the claimed alternate glucose pathway.

While it is mandatory to select glucose and a component that has equal ability to flow within the BBB and the CSF, is an insulin counterregulatory hormone and is not produced by the brain, to show the presence of the claimed glucose pathway, the use of other components found in CSF is also within the scope of this invention. Another method, hereinafter identified as method two, of proving the existence of the alternate glucose pathway comprises: introducing an Ommaya reservoir into the intraventricular spaces of the brain of an animal, preferably a non-human primate; starting a positron emission tomography (PET) scan on the animal; drawing a desired amount of cerebral spinal fluid (CSF) from the Ommaya reservoir, the amount of equal volume as the amount of 2-deoxy-2-[18F] fluoro-D-Glucose, hereinafter referred to as $^{18}$FDG, to be injected subsequently into the Ommaya reservoir; and, injecting a desired amount of a radioactive compound, 0.03–0.05 mCi/kg of $^{18}$FDG, preferably 0.04 mCi/kg of $^{18}$FDG, diluted from a stock solution with a solution isotonic to CSF into the Ommaya reservoir until the PET scan detects radioactivity in the surface of the cortex in the brain and the spine. mCi is millicurie.

Detection of radioactivity in the cortex of the brain and the spine proves the presence of the alternate glucose pathway. The above method does not require the sacrifice of the animal. An alternate method, requiring the sacrifice of the animal, however, can more strongly prove the presence of the alternate glucose pathway. This method does not employ PET scan but rather uses autoradiography. This alternate method comprises instead, injecting a desired amount of a radioactive compound, preferably 40 uCi (microcurie)/kg of 2-deoxy-D[$^{14}$C] glucose, hereinafter referred to as [$^{14}$C] DG, into the Ommaya reservoir; isolating the brain of the non-human primate; detecting presence of radioactivity on the cortex layer I–III of the brain by autoradiography.

To improve the sensitivity of the PET scan above, the following additional steps should be undertaken: withdrawing a second sample of CSF from the Ommaya reservoir; injecting a low dose of insulin, preferably at approximately 100 microunit/kg and $^{18}$FDG at approximately 0.03–0.05 mCi/kg into the Ommaya reservoir; observing any changes in the PET scan; injecting a desired amount of cortisol, preferably at one milligram and $^{18}$FDG at same concentration as above into the Qmmaya reservoir after the insulin infusion; and, observing any changes in the PET scan.

Having the information of the above alternate glucose pathway, several diagnostic tools for detecting mental disorders as well as nondetectable neurological disorders can be derived. This is made possible because in the claimed alternate glucose pathway, glucose pass through the CSF to the Cortex I–III, and possibly IV, thereby affecting those cell layers which is different from the presently accepted second pathway. Using a similar scheme as method two above, a profile for each mental disorder has first to be established. The method for establishing a profile for each mental disorder as well as for the nondetectable neurological disorders, herein disorders, is based on observing the effect of artificially induced chemical imbalance in the CSF and consequently the brain and the spine, and on the plasma and urine after a desired compound, hereinafter referred to as biological marker, is infused into the CSF through the Ommaya reservoir. The CSF, urine and plasma are referred to herein as biological fluids.

The method of establishing a diagnostic profile for a disorder at the different age group, comprises: a) introducing an Ommaya reservoir into the anterior horn of the lateral ventricule of the brain, a subarachnoid catheter on the brain, a spinal catheter on the spine, intracranial pressure catheter at the CSF, a Foley catheter at the bladder, a central catheter in either the jugular or femoral vein of an animal, preferably a non-human primate, the non-human primate selected for the different age group being tested; b) starting a positron emission tomography (PET) scan on the animal; c) drawing a desired amount preferably 6 milliliter (ml) of cerebral spinal fluid (CSF) from the Ommaya reservoir, and subarachnoid catheter of a normal functioning brain, a desired amount of CSF, preferably 3 ml from the spinal region of a normal functioning spine; d) drawing blood, preferably 10 ml from either the jugular or femoral vein; e) drawing urine, preferably 10 ml from the bladder; f) measuring each desired biological marker/s present in the CSF namely glucose, metabolites, neurotransmitters, neuropeptides, insulin, immune globulins, counterregulatory hormones, neuronal growth factors, thyroid hormones, other hormones found in the CSF, and peptidases on the CSF, plasma and urine drawn above for a baseline data; g) measuring electroencephalogram activities (hereinafter also referred to as EEG) of the brain; h) measuring intracranial pressure (also referred to herein as ICP) at the CSF; i) injecting approximately 0.02 mCi/kg (kilogram) of $C^{11}$ labeled biological marker, also referred to herein as radioactive biological marker, into the Ommaya reservoir for the determination of the time before the first sample is taken for testing; j) infusing five times the baseline amount as determined for each of the biological marker from step f) for each of the non radioactive biological marker into the Ommaya reservoir over a 6 hour period to artificially induce a diseased state; k) continuing the infusion at this elevated amount for each 6 hour interval for a total of one week; and, 1) withdrawing a CSF sample from the Ommaya reservoir and the subarachnoid and spinal catheters equivalent in amount as the infused volume in step i) for the first sample and step j) for the subsequent samples, urine from the Foley catheter and plasma from the central catheter at the time the radiolabeled biological marker reaches the cortex and every six hours thereafter and at the completion of infusion of each biological marker; m) determining the effect of each infusion of a biological marker from step j) to the level of all the biological markers at those time intervals; and, n) graphing for each time interval taken, the levels of the different biological markers at each infusion of a biological marker from step j) for each age group; and, o) repeating the process, a) to n), for each biological marker thereby obtaining a diagnostic profile on the effect of each biological marker infused at five times the normal level on the level of all the biological markers present in the CSF.

The time interval it takes for the biological marker to reach the cortex is determined by the travel time of the radioactive biological marker from the ventricle to the surface of the brain bathed in the CSF as determined by PET scan. This is the time between the injection at the ventricle to the time the cortex projects an image. Each biological marker will have their own travel time.

After the diagnostic profile in non-human primate is determined as described above, the following steps are done on humans: a) drawing normal human CSF samples, usually 3 ml, by a spinal tap from different age groups for determining a normal level for each biological marker at the different age groups; b) drawing human CSF samples, usually 3 ml by a spinal tap from diseased patients, patients with mental disorders and nondetectable neurological disorders, from different age groups for determining a diseased level for each biological marker at the different age groups; c) graphing the levels of the different biological markers obtained from a normal and a diseased patients; d) discarding the biological marker where the normal level of the animal, a non-human primate, is different from the normal level of a human patient; e) comparing the graph of the normal patient and the graph of the diseased patient with the graph obtained from the non-human primate; f) choosing the graph of the non-human primate that comes closest to the graph of the normal and diseased patient; g) determining the biological marker in the non-human primate that produced the same graph as the diseased human patient; and, h) diagnosing the disorder of the diseased human patient based on the biological marker determined from step g).

The series of graphs obtained above is categorized for each disorder at each state and each age groups.

The above test offers an objective method of determining the particular disorder of the patient which until now is mostly determined by their actions and outward appearance and behavior. The above process likewise establishes an information bank of diagnostic profiles for each biological marker from which various diagnostic tool or test can be further derived or developed. If the patient's profile does not match any of the diagnostic profiles obtained from non-human primates for the suspected disorder, the causative biologic marker must be one of those initially discarded from further evaluation because the normal levels of the non-human primate did not match the normal levels of the normal human patient or the causative agent or biological marker was not tested.

An example of a diagnostic tool or test for a disease state that is derived through the existence of the claimed alternate glucose pathway and the above diagnostic profile is the test for Alzheimer Disease. Using this test or diagnostic tool, a diseased human patient with Alzheimer disease will show when graphed, an elevated cortisol in the CSF and in the urine with a moderate elevation in the plasma associated with, for example, an increase in the tau protein, a decrease in somatostatin and peptide histidine methionine.

The elevated cortisol level in CSF is explained by the proposed alternate glucose pathway. Since cortisol can flow equally well within the BBB and through the CSF, the current second pathway, is unable to explain the observed elevated level of cortisol because if the current second pathway is true, the cortisol concentration in the CSF will not increase because the CSF is not a major component within that glucose pathway. In the current glucose pathway, the cortisol is expected to pass within the BBB, to the brain which would eventually be excreted by the kidneys. In the claimed invention, the concentration of cortisol in CSF and for that matter, other components of CSF, can increase because it takes time before the CSF goes back to the blood circulation which delays the excretion of the CSF component through the kidneys. In the current second pathway, without the CSF directly in the pathway, there will be no factor to delay the excretion of cortisol through the kidneys. With the claimed pathway, when insulin binds to the insulin receptors found on the cell membrane of cells found within the cortex layer I–III, this triggers a signal to the gene located in the nucleus to transcribe glucose transporters thereby increasing the number of glucose transporters on the cell membrane. The increase in glucose transporters will allow more glucose to enter the cells located in the cortex cell layer I–III of the brain. In Alzheimer Disease where cortisol level is high in the CSF, the effect of cortisol is opposite that of insulin. Cortisol desensitizes the insulin receptors thereby unabling it to bind with insulin. Because the insulin can not bind to the receptor, additional glucose transporters are not transcribed at the cell membrane thereby causing a low glucose level in the cells located in the cortex cell layer I–III and possibly cortex layer IV of the brain, a phenomena observed in Alzheimer disease. This observation of low glucose concentration in the cortex cell layer I–III and high level of cortisol in the CSF interrelates the presence of the alternate glucose pathway and the used of this principle, that of acknowledging the importance of CSF in diagnosing the disorders.

As mentioned above, there are disorders that can not be adequately diagnosed using the diagnostic profile or test described above because the causative agents were not tested and graphed. Examples of these are bacteria, fungi, proteins and allergens which are not expected to be found or present only in minimal amounts in the CSF and other causative agents such as white blood cells and red blood cells which can not be detected through the PET scan. Following the teachings of the presence of the alternate glucose pathway and the major role played by the CSF in this pathway, a CSF sample should be taken and tested for these causative agents in cases where no match between the non-human primate graphs and those of the diseased human patient is found. The current practice of testing just the plasma and urine will be inadequate because the causative agent has to enter the CSF to affect the brain. Consequently, once the causative agent is found in the CSF, a medication can be directly introduced to the CSF for immediate response.

Adopting the alternate glucose pathway and the insulin pathway proposed by the claimed invention and using the test described, medications for patients who suffer mental and nondetectable neurological disorders can be developed. Biological markers that cause mental disorders and nondetectable neurological disorders affect the cortex cell layer I–III, possibly IV, in the brain and the spine.

It is expected that some disorders will show either an abnormally elevated biological marker/s or the presence of these biological markers which is/are otherwise absent in the CSF. For these situations, a medication that binds, reduces or eliminates the biological marker has to be introduced to the CSF to reduce or remove this from circulation. However, for biological markers that are abnormally reduced from normal or absent in the CSF but otherwise has to be present, a medication that elevates this biological marker to normal levels can be introduced to the CSF. The preferred medication should be one that has the ability to cross both the blood side and the brain side of the BBB, in the same manner as the glucose transport in the alternate glucose pathway, to the cortex layer I–III because these types of medication can be administered orally, intramascularly or intravenously. However, if the medication does not have this ability, it can still be used by directly introducing this into the CSF by injection or infusion.

The following is an example that demonstrate the need of a medication or mode of treatment described above. In Alzheimer's disease, the cortisol concentration in CSF is high while some neuropeptides will test lower than or higher than normal. Because of this high level of cortisol in the CSF, the beta-amyloid precursor (protein beta APP), and the tau protein found in the enthorhinal cortex layer II–IV are non functional. This phenomena can be explained by the alternate glucose pathway and the insulin pathway because the elevated cortisol depresses or makes unavailable the required glucose by the brain. This reduced glucose level results in a decrease of available adenosine triphosphate (ATP), consequently, the rate of metabolism is affected which impacts the normal functioning of protein beta-APP and tau protein. This reduced glucose level also cause the observed cell shrinkage within the cortex layer I–III, possibly IV, in Alzheimer's disease.

While the embodiment of the present invention has been described, it should be understood that various changes, modifications and adaptations may be made therein without departing from the spirit of the invention and the scope of the appended claims. Those skilled in the art will recognize that other and further variations of the values presented herein are possible. The scope of the present invention should be determined by the teachings disclosed herein, the appended claims and their legal equivalents.

I claim:

1. A method of detecting Alzheimer disease in a patient, comprising:
   measuring a level of cortisol in the cerebro-spinal fluid (CSF) of the patient,
   comparing the level of cortisol with a normal level in a non-diseased human, and
   detecting an elevated cortisol level, so as to identify Alzheimer disease in the patient.

* * * * *